(12) United States Patent
Pauley et al.

(10) Patent No.: US 11,766,198 B2
(45) Date of Patent: Sep. 26, 2023

(54) LIMB-WORN PATIENT MONITORING DEVICE

(71) Applicant: Cercacor Laboratories, Inc., Irvine, CA (US)

(72) Inventors: Kevin Hughes Pauley, Lake Forest, CA (US); Hung The Vo, Fountain Valley, CA (US); Mathew Paul, Irvine, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 332 days.

(21) Appl. No.: 16/265,733

(22) Filed: Feb. 1, 2019

(65) Prior Publication Data
US 2019/0239787 A1    Aug. 8, 2019

Related U.S. Application Data

(60) Provisional application No. 62/625,475, filed on Feb. 2, 2018.

(51) Int. Cl.
| | | |
|---|---|---|
| *A61B 5/1455* | (2006.01) | |
| *A61B 5/00* | (2006.01) | |
| *A61B 5/0205* | (2006.01) | |
| *A61B 5/024* | (2006.01) | |

(Continued)

(52) U.S. Cl.
CPC ........ *A61B 5/14552* (2013.01); *A61B 5/0205* (2013.01); *A61B 5/6802* (2013.01); *A61B 5/6824* (2013.01); *A61B 5/6828* (2013.01); *A61B 5/6838* (2013.01); *A61B 5/002* (2013.01); *A61B 5/021* (2013.01); *A61B 5/029* (2013.01);

(Continued)

(58) Field of Classification Search
CPC ............... A61B 5/6802; A61B 5/6824; A61B 5/6838; A61B 5/0205; A61B 5/6828; A61B 2562/0238; A61B 5/002; A61B 5/021; A61B 5/029; A61B 5/02405; A61B 5/145

See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |

(Continued)

OTHER PUBLICATIONS

US 2022/0192529 A1, 06/2022, Al-Ali et al. (withdrawn)

(Continued)

*Primary Examiner* — Eric F Winakur
*Assistant Examiner* — Abid A Mustansir
(74) *Attorney, Agent, or Firm* — Knobbe Martens Olson & Bear LLP

(57) ABSTRACT

The present disclosure describes example systems, methods, apparatuses, and medical devices for obtaining physiological parameter data from a wearable patient monitoring device. An example patient monitoring device can include an emitter and a detector. The emitter can emit light through tissue of a patient. The detector can sense the light after it passes through and is attenuated by the tissue and can generate a signal indicative of the sensed light. When the patient monitoring device is attached to or worn by the patient, the emitter and detector are aligned such that the light from the emitter travels through an opening between a first bone and a second bone of the patient prior to being sensed by the detector.

19 Claims, 8 Drawing Sheets

(51) Int. Cl.
*A61B 5/021* (2006.01)
*A61B 5/029* (2006.01)

(52) U.S. Cl.
CPC ... *A61B 5/02405* (2013.01); *A61B 2562/0238* (2013.01)

(56) References Cited

U.S. PATENT DOCUMENTS

| | | | |
|---|---|---|---|
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| 5,402,777 A * | 4/1995 | Warring | A61B 5/02433 |
| | | | 424/449 |
| D359,546 S | 6/1995 | Savage et al. | |
| 5,431,170 A | 7/1995 | Mathews | |
| 5,436,499 A | 7/1995 | Namavar et al. | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A * | 6/1997 | Diab | A61B 5/02427 |
| | | | 356/41 |
| 5,645,440 A | 7/1997 | Tobler et al. | |
| 5,671,914 A | 9/1997 | Kalkhoran et al. | |
| 5,685,299 A | 11/1997 | Diab et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,987,343 A | 11/1999 | Kinast | |
| 5,995,855 A | 11/1999 | Kiani et al. | |
| 5,997,343 A | 12/1999 | Mills et al. | |
| 6,002,952 A | 12/1999 | Diab et al. | |
| 6,010,937 A | 1/2000 | Karam et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,040,578 A | 3/2000 | Malin et al. | |
| 6,045,509 A | 4/2000 | Caro et al. | |
| 6,066,204 A | 5/2000 | Haven | |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |

(56) References Cited

U.S. PATENT DOCUMENTS

| | | |
|---|---|---|
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |

(56) References Cited

U.S. PATENT DOCUMENTS

| | | |
|---|---|---|
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |

(56) References Cited

U.S. PATENT DOCUMENTS

| | | | |
|---|---|---|---|
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,938,279 B1 * | 1/2015 | Heaton, II ............ A61B 5/1455 600/323 |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |

(56) References Cited

U.S. PATENT DOCUMENTS

| | | |
|---|---|---|
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,730,644 B1 * | 8/2017 | Wu ............... A61B 5/7278 |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |

(56) References Cited

U.S. PATENT DOCUMENTS

| | | |
|---|---|---|
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0343371 A1* | 11/2014 | Sowers, II ......... A61B 5/02141 600/301 |
| 2014/0357966 A1 | 12/2014 | Al-Ali et al. |
| 2014/0358012 A1* | 12/2014 | Richards ............. A61B 5/6802 600/479 |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |

(56) References Cited

U.S. PATENT DOCUMENTS

| | | |
|---|---|---|
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0007925 A1* | 1/2016 | Mirov .................. G01B 11/14 356/400 |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0046048 A1* | 2/2019 | Kitagawa ............. A61B 5/6843 |
| 2019/0117070 A1 | 4/2019 | Muhsin et al. |
| 2019/0200941 A1 | 7/2019 | Chandran et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0000345 A1* | 1/2020 | Connor ................ A61B 5/0205 |
| 2020/0021930 A1 | 1/2020 | Iswanto et al. |
| 2020/0060571 A1* | 2/2020 | Dauguet ............... A61B 5/6843 |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |

(56) References Cited

U.S. PATENT DOCUMENTS

| | | |
|---|---|---|
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0058843 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |

OTHER PUBLICATIONS

Nitzan M, Romem A, Koppel R. Pulse oximetry: fundamentals and technology update. Med Devices (Auckl). 2014;7:231-239 https://doi.org/10.2147/MDER.S47319 (Year: 2014).*

* cited by examiner

LIMB-WORN PATIENT MONITORING DEVICE

CROSS-REFERENCE TO RELATED APPLICATIONS

The present application claims priority benefit to U.S. Provisional Application No. 62/625,475, entitled "Wrist-Worn Patient monitoring device," filed Feb. 2, 2018, which is hereby incorporated herein by reference in its entirety.

TECHNICAL FIELD

The present disclosure relates generally to the field of patient monitoring devices. In particular, the present disclosure relates to a patient monitoring device configured to be worn on a limb of a patient, such as an arm or a leg.

BACKGROUND

Pulse oximetry is a widely accepted noninvasive procedure for measuring the oxygen saturation level of arterial blood, an indicator of a person's oxygen supply. A typical pulse oximetry system utilizes a sensor applied to tissue of a patient. The sensor includes emitters that transmit optical radiation into the tissue. A detector receives the optical radiation after it is attenuated by pulsatile arterial blood flowing within the tissue, and the detector generates a signal responsive to the received optical radiation. Based at least in part on the signal generated by the detector, a processor can determine one or more physiological parameters, such as blood oxygen saturation ($SpO_2$), pulse rate (PR), pulse rate variability (PRV), etc., or can cause a display to display visual indications, such as plethysmograph waveform.

Noninvasive blood parameter monitors capable of measuring blood parameters in addition to $SpO_2$, such as carboxyhemoglobin (HbCO), methemoglobin (HbMet) and total hemoglobin (Hbt) and corresponding multiple wavelength optical sensors are available from Cercacor Laboratories, Inc. ("Cercacor") of Irvine, Calif. Noninvasive blood parameter monitors and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Cercacor and both incorporated by reference herein.

SUMMARY

The present disclosure describes example systems, methods, apparatuses, and medical devices for obtaining physiological parameter data from a wearable patient monitoring device. An example patient monitoring device according to the present disclosure can include a wearable housing, an emitter, a detector, a first resilient member, and a second resilient member. The wearable housing can be attached at least partially around a forearm of a patient, and the wearable housing can support at least one of the emitter, the detector, the first resilient member, or the second resilient member. The emitter can emit light through tissue of the forearm, and the detector can sense the light after it passes through and is attenuated by the tissue and generate a signal indicative of the sensed light. The first resilient member can exert a first force on the emitter. The force can be in a direction of the tissue with respect to the emitter. The second resilient member can exert a second force on the detector. The second force can be in a direction of the tissue with respect to the detector. When the housing is worn by the patient, the emitter and detector are aligned such that the light from the emitter travels through an opening between radial and ulnar bones of the forearm prior to being sensed by the detector.

The present disclosure also provides an example patient monitoring device. The example patient monitoring device can include an emitter and a detector. The emitter can emit light through tissue of a patient. The detector can sense the light after it passes through and is attenuated by the tissue and can generate a signal indicative of the sensed light. When the patient monitoring device is attached to or worn by the patient, the emitter and detector are aligned such that the light from the emitter travels through an opening between a first bone and a second bone of the patient prior to being sensed by the detector.

The example patient monitoring device of any of the preceding paragraphs may also include any combination of the following features described in this paragraph, among others described herein. The tissue can correspond to a forearm of the patient, the first bone can include a radial bone of the forearm, and the second bone can include an ulna bone of the forearm. The tissue can correspond to a lower leg of the patient, the first bone can include a tibia bone of the lower leg, and the second bone can include a fibula bone of the lower leg. The emitter can be proximate to the tissue relative to the detector. The device can further include a resilient member that exerts a force on at least one of the emitter or the detector. The force can be in a direction of the tissue with respect to the at least one of the emitter or the detector. The resilient member can include a spring coupled to the at least one of the emitter or the detector. The resilient member can include an inflatable bladder that, when inflated, can secure the at least one of the emitter or the detector to the tissue.

The example patient monitoring device of any of the preceding paragraphs may also include any combination of the following features described in this paragraph, among others described herein. The device can include a hinge on which at least a portion of the patient monitoring device is configured to swing. The patient monitoring device can attach completely around at least one of a forearm of the patient or a lower leg of the patient. A shape of the patient monitoring device can include at least one of an oval-shape or an elliptical shape. The shape of the patient monitoring device can limit radial movement about forearm of the patient. The detector can include a large area photodetector.

The example patient monitoring device of any of the preceding paragraphs may also include any combination of the following features described in this paragraph, among others described herein. The emitter can be a first emitter and the light can be first light. The device can further include a second emitter configured to emit second light towards the tissue. The detector can detect the second light after it is reflected, refracted, or both by the tissue and can generate a signal indicative of the sensed second light. The second emitter can consume less energy than the first emitter.

The present disclosure also provides a method of determining a physiological parameter. The method can include receiving a signal corresponding to a transmission pulse oximetry system of a wearable patient monitoring device. The transmission pulse oximetry system can include an emitter configured to emit light through tissue of a patient. The transmission pulse oximetry system can further include a detector configured to sense the light after it passes through and is attenuated by the tissue and to generate the signal indicative of the sensed light. When the wearable patient monitoring device is worn by the patient, the emitter and detector are aligned such that the light from the emitter travels through an opening between a first bone and a second bone of the patient prior to being sensed by the detector. The method can further include determining a physiological parameter based at least in part on the signal.

The method of the preceding paragraph may also include any combination of the following features or steps described in this paragraph, among others described herein. The signal can be a first signal, the emitter can be a first emitter, and the light can be first light. The method can further include receiving a second signal corresponding to a reflective pulse oximetry system of the wearable patient monitoring device. The reflective pulse oximetry system can include a second emitter configured to emit second light to the tissue of a patient. The reflective pulse oximetry system can further include the detector. The detector can be further configured to sense the second light after it is reflected and/or refracted at the tissue prior to being received by the detector and to generate the second signal indicative of the sensed second light. Said determining the physiological parameter can be further based at least in part on the second signal.

The method of any of the preceding two paragraphs may also include any combination of the following features or step described in this paragraph, among others described herein. The second emitter can consume less energy than the first emitter. The tissue can correspond to a forearm of the patient, the first bone can include a radial bone of the forearm, and the second bone can include an ulna bone of the forearm. The tissue can correspond to a lower leg of the patient, the first bone can include a tibia bone of the lower leg, and the second bone can include a fibula bone of the lower leg. The detector can include a large area photodetector.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

The following drawings and the associated descriptions are provided to illustrate embodiments of the present disclosure and do not limit the scope of the claims.

Figure 1:
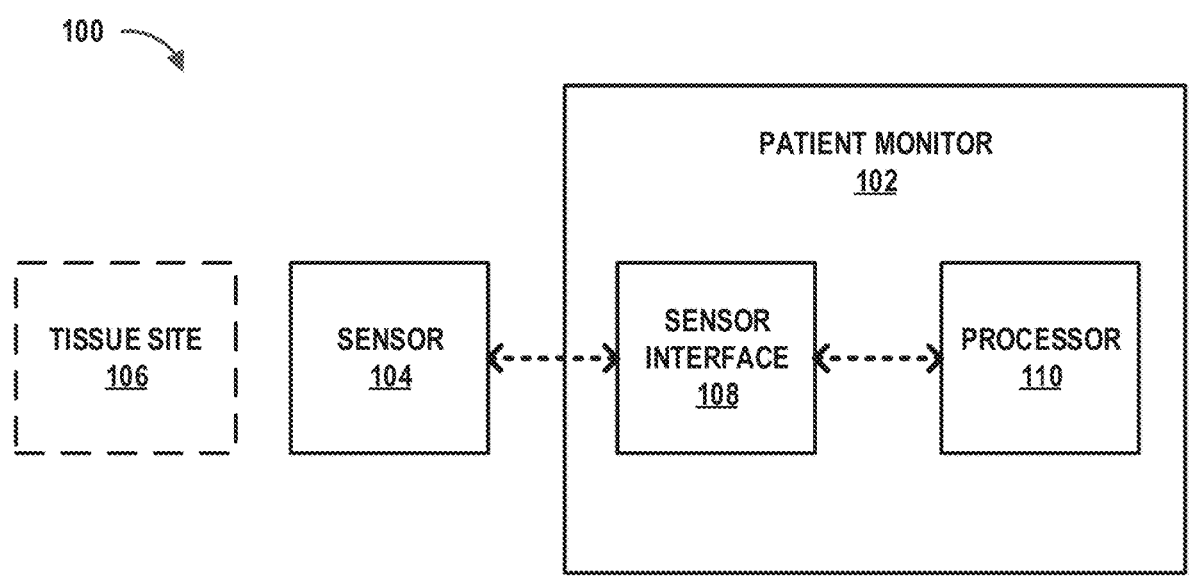
FIG. 1 illustrates a block diagram of an example patient monitoring system.

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

Overview

Beer's Law (also known as the Beer-Lambert Law) relates the attenuation of light to properties of the material through which the light is traveling. In particular, Beer's law states that the absorbance of a material is proportional to both the length of the light path through the material and the concentrations of the attenuating species in the material. The relationship between these parameters can be expressed as:

$$A = \epsilon b^* c \quad \text{(Equation 1)}$$

where A is the absorbance of the material at a given wavelength of light, $\epsilon$ is the molar absorptivity or extinction coefficient (in L mol$^{-1}$ cm$^{-1}$), unique to each molecule and varying with wavelength, b is the length of the light path through the material (in cm), and c is the concentration of an analyte of interest (in mol L$^{-1}$). As illustrated by Equation 1, the absorbance of a material can be affected by the length of the light path through the material (sometimes referred to as pathlength).

Pulse oximetry measurements can be taken on a patient's fingertip. For example, a fingertip pulse oximeter can be clipped onto the patient's finger to obtain the measurements. In some cases, however, wearing a fingertip pulse oximetry sensor can at least temporarily restrict the patient from performing daily activities. For example, a fingertip pulse oximeter may be connected to a patient monitor, which can limit a patient's ability to move. As another example, in some cases, a fingertip pulse oximeter can be prone to slip off a patient's finger if the patient moves around, which can cause inaccurate or null measurements. Further still, in some cases, the mere placement of the sensor onto the fingertip can restrict the patient's ability to perform typical hand functions, such as grasping or holding objects. Accordingly, in some cases, it can be advantageous to obtain a pulse oximetry measurement at other measurement sites, such as on a patient's forearm, lower leg, or the like.

In some cases, determining a physiological parameter from a pulse oximetry measurement at a measurement site other than the fingertip can be more complicated that determining the physiological parameter from a pulse oximetry measurement at the fingertip. For example, a finger, a forearm, and a lower leg are each different in both shape and size. For instance, a forearm and/or a lower leg can be magnitudes larger than a finger. As a result, a pathlength associated with a forearm and/or a pathlength associated with a lower leg can be an order of magnitude higher than a pathlength associated with a fingertip. In some cases, as the pathlength increases, so do the complexities associated with accurately determining a physiological parameter. For example, a larger pathlength can result in higher absorption effects, which can necessitate a higher intensity of the light transmitted through the material. As another example, larger pathlength can result in higher scattering effects, which can increase an area over which the light scatters.

Furthermore, a bone layout of a measurement site can also present obstacles in accurately determining a physiological parameter. For example, in some cases, light that is transmitted into a tissue site can collide with one or more bones, which can result in inaccurate measurements. As an example, the forearm includes the radius and ulna bones, while the lower leg includes the tibia and the fibula bones.

In addition, a length or curvature of the measurement site can present obstacles in accurately determining a physiological parameter. For example, due to the length and/or curvature of a forearm, when a patient monitoring device is worn on the forearm, it may be susceptible to movement (e.g., sliding along the forearm or rotating about the forearm), which can cause misalignment of the emitter and detector, and ultimately an inaccurate determination of the physiological parameter. Similarly, due to the length and/or curvature of a lower leg, when a patient monitoring device is worn on the lower leg, it may be susceptible to movement (e.g., sliding along the lower leg or rotating about the lower leg), which can cause misalignment of the emitter and detector, and ultimately an inaccurate determination of the physiological parameter.

Embodiments of the patient monitoring device described herein can address these and other obstacles. For example, in some embodiments, a patient monitoring device can be configured to be worn on a limb of a patient, rather than a fingertip, which can improve a mobility of the patient monitoring device. For instance, the patient monitoring device can be configured to be worn on a wrist, a forearm, an elbow, an upper arm, an ankle, a lower leg, a knee, or an upper leg.

In some cases, the patient monitoring device can include an emitter and a detector that are aligned such that the light from the emitter completely or substantially avoids a collision with a bone prior to being sensed by the detector. For example, if the measurement site corresponds to a forearm, when the patient monitoring device is attached to the forearm the emitter and detector can be aligned such that the light from the emitter travels through an opening between radial and ulnar bones of the forearm prior to being sensed by the detector. As another example, if the measurement site corresponds to a lower leg, when the patient monitoring device is attached to the lower leg the emitter and detector can be aligned such that the light from the emitter travels through an opening between tibia and fibula bones of the lower leg prior to being sensed by the detector.

Furthermore, the patient monitoring device can include features that can limit lateral movement along or rotational movement about the patient's limb, which can reduce a likelihood of misalignment of the emitter and detector. For instance, the patient monitoring device can include a housing configured to fit securely on the patient's limb. As another example, the patient monitoring device can have an oval or elliptical shape, which can decrease a likelihood of movement about the patient's limb.

As another example, the patient monitoring device can include features configured to facilitate a coupling between the emitter or detector and the patient skin, which can increase a likelihood receiving a signal without motion artefacts. For example, the patient monitoring device can include a resilient member that can facilitate good coupling between the emitter and the patient's skin and/or the detector and the patient's skin.

In some cases, the detector can be implemented as a Large Area Detector (LAD), which can allow the detector to sense the light emitted from the emitter despite the increased scattering effects of the increases pathlength. In some cases, The larger surface area of the LAD can allow the detector to gather light scatter over a larger area, which can improve a reliability of the received signal and, ultimately, the accuracy of the physiological data.

System Overview

FIG. 1 illustrates a block diagram of an example patient monitoring system 100. The patient monitoring system 100 includes a patient monitor 102 communicatively coupled to a sensor 104. As illustrated, the patient monitor 104 can include a processor 110 and a sensor interface 108. During use, the sensor 104 can be proximate a tissue site 106. As described herein, the sensor 104 can generate a signal indicative of one or more physiological parameters of the patient.

A sensor type of the sensor 104 can vary across embodiments. For example, the sensor 104 can include, but is not limited to, an optical coherence tomography (OCT) device, a spectrometer, a pulse oximetry device, a plethysmograph sensor, a pressure sensor, an electrocardiogram sensor, or an acoustic sensor, among other sensors.

In some cases, the sensor 104 is a single sensor. Alternatively, the sensor 104 can include multiple sensors, such as multiple pulse oximetry sensors. For example, sensor 104 can include a first pulse oximetry sensor configured for transmittance pulse oximetry and a second pulse oximetry sensor configured for reflectance pulse oximetry. In some cases, the sensor 104 can include a single pulse oximetry sensor configured for both reflectance and transmittance pulse oximetry. In instances in which sensor 104 includes multiple sensors, the sensor 104 can be used to detect physiological parameters at the same or a proximate tissue site. For example, each sensor 104 can obtain measurements at the same tissue site 106. Alternatively, in some cases, the sensors 104 can obtain measurements at different tissue sites.

As described herein, the tissue site 106 can include, but is not limited to, a wrist, a forearm, an elbow, and upper arm, an ankle, a lower leg, a back of the knee, or an upper leg. In some cases, the sensor 104 and/or at least a portion of the patient monitor 102 can be integrated into an apparatus that can be worn by the patient, for example, on or proximate to the tissue site 106. For example, the apparatus can include, but is not limited to, an arm band, a watch, a bracelet, a sleeve, a glove, a sock, an anklet, a wrap, or another apparatus that can be worn or attached to the tissue site 106.

The patient monitor 102 can include a sensor interface 108 and a processor 110. In some cases, the sensor interface 108 can communicate with the sensor 104. For example, the sensor interface 108 can collect data from the sensor 104 and can output data to the processor 100. For instance, the sensor interface 108 can include a front end component, such as the front end component 214 of FIG. 2. As another example, the sensor interface 108 can provide control signals to the sensor 104. For instance, the sensor interface 108 can include drivers or multiplexers, such as the driver(s)/multiplexer(s) 216 of FIG. 2.

The patient monitor 102 can be in communication with the sensor 104. For example, the patient monitor 102 can receive a signal from the sensor 104 and can determine, based at least in part on the received signal, one or more physiological parameters, such as, but not limited to, blood oxygen saturation ($SpO_2$), pulse rate (PR), pulse rate variability (PRV), SpHb®, SpOC™, PVi®, SpMet®, SpCO®, or RRa®. In some cases the physiological parameter can include a concentration of an analyte, pulse pressure variation (PPV), stroke volume (SV), stroke volume variation (SVV), mean arterial pressure (MAP), central venous pressure (CVP), HbCO, HbMet, or Hbt, among other parameters. Further, in some cases, the patient monitor 102 can derive one or more relationships from the determined parameters, and the patient monitor 102 can utilize the relationships to determine other parameters, such as the patient's glucose levels, systemic vascular resistance (SVR), CO, or arterial blood pressure (BP).

The patient monitor 102 can be communicatively coupled to the sensor 104. For example, the patient monitor 102 can receive a signal from the sensor 104. The received signal may take various forms, such as a voltage, a current, or charge. An operational amplifier (op-amp) of the patient monitor 102 can increase the amplitude, as well as transform the signal, such as from a current to a voltage. An anti-aliasing filter (AAF) of the patient monitor 102 can then process of the output signal from the op-amp to restrict a bandwidth of the output signal from the op-amp to approximately or completely satisfy the sampling theorem over a band of interest. An analog-to-digital convertor (ADC) of the patient monitor 102 can convert the output signal from the AAF from analog to digital. The output signal from the ADC can then be sampled by a processor of the patient monitor 102 at a relatively high speed. The result of the sampling can next be downsampled by a processor of the patient monitor 102, before waveform analysis may be performed by a DSP.

Figure 2:
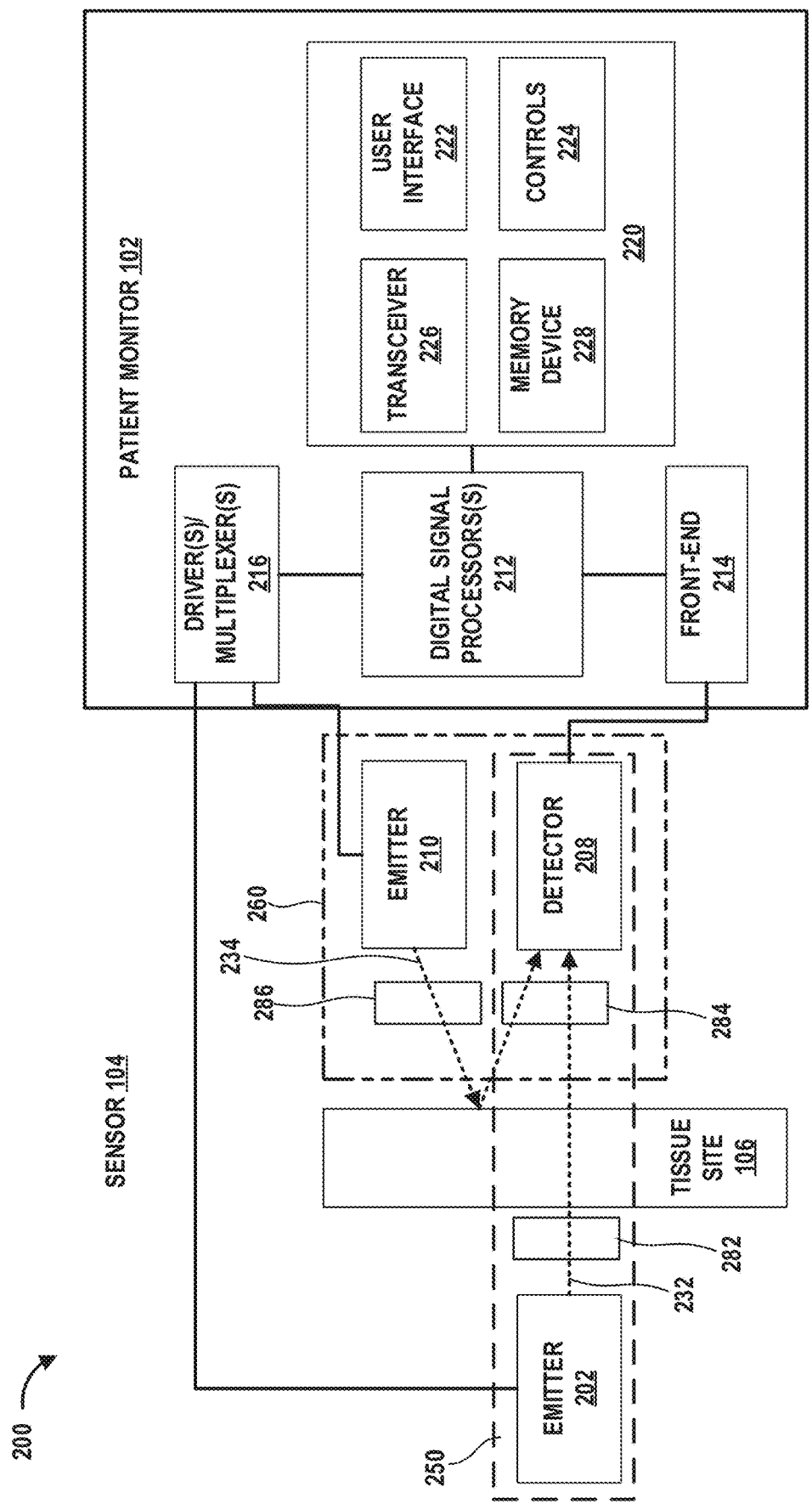
FIG. 2 illustrates a block diagram of an example patient monitoring system.

FIG. 2 illustrates a block diagram of an example patient monitoring system 200, which can be an embodiment of the patient monitoring system 100. As illustrated, the patient monitoring system 200 includes a patient monitor 102 and a sensor 104. In this example the patient monitor 102 includes a digital signal processor (DSP) 212, drivers/multiplexer 216, a front end 214, and one or more input or output devices 220. Furthermore, the sensor 104 includes emitters 202, 210 and detector(s) 208 (e.g., photo diode, photo detector, etc.). As described herein, the sensor 104 can obtain measurements from the tissue site 106.

In some cases, the sensor 104 can include a transmission pulse oximetry system 250 configured for transmission pulse oximetry. For example, the transmission pulse oximetry system 250 can include an emitter 202 and a detector 208. The emitter 202 can emit light 232 through the tissue site 106. The detector 208 can sense the light 232 emitted by the emitter 202 after it passes through and is attenuated by the tissue site 106. Furthermore, the detector 208 can generate one or more composite analog light intensity signals responsive to the light 232 sensed by the detector 208. As illustrated in FIG. 2, in some cases, the detector 208 is proximate the tissue site 106 relative to the emitter 202. For example, if the tissue site 106 is a forearm, the detector 208 can be positioned on one side of the forearm and the emitter 202 can be positioned on an opposite side of the forearm.

As described herein, the tissue site 106 may be associated with a larger pathlength than a pathlength associated with a fingertip. This is due at least in part to the increased thickness of the tissue site 106. For example, a forearm and/or a lower leg can be magnitudes larger than a finger. As a result, a pathlength associated with a forearm and/or a pathlength associated with a lower leg can be an order of magnitude higher than a pathlength associated with a fingertip. The light 232 emitted by the emitter 202 can include one or more wavelengths of light. For example, the emitter 202 can emit red light (e.g., approximately 660 nm), infrared light (e.g., approximately 905 nm), near-infrared light, or other wavelengths. In some cases, the larger pathlength can result in higher absorption effects, which can necessitate a relatively higher intensity of the light transmitted through the tissue site 106. Accordingly, in some cases, the emitter 202 can include a plurality of LEDs connected in series so as to generate sufficient light to traverse through the tissue site 106. Furthermore, in some cases, lower wavelengths can be more susceptible to attenuation or absorption over the large pathlength. For example, due to the higher absorption at Red compared to Infrared, the emitter 202 can include multiple Red LEDs connected in series, which can help the emitter 202 generate sufficient light to traverse through the tissue site 106.

As described herein, in some cases, the larger pathlength can result in higher absorption effects. In some cases, the detector 208 can gather light scatter over a large area, which can improved the signal generated by the detector 208. For example, the detector 208 can be implemented as a Large Area Detector (LAD), which can be used to integrate light over a larger area as compared to a traditional detector.

In some cases, the sensor 104 and/or the transmission pulse oximetry system 250 can include one or more optical elements to increase an amount of light 232 that reaches the detector 208. For example, as illustrated in FIG. 2, the sensor 104 can include a lens 282 positioned between the emitter 202 and the tissue site 106. In some cases, at least some of the light 232 from the emitter 202 passes through the lens 282 and the lens 282 focuses the light 232, thereby increasing strength of the signal and the amount of light 232 that reaches the detector 208. It will be understood that other optical elements can be utilized to increase the strength of one or more intensity signals emitted by the emitter 202. For example, in some cases, multiple lenses or one or more meta-materials can be positioned between the emitter 202 and the tissue site 106 to increase an amount of light received by the detector 208.

As another example, the sensor 104 and/or the transmission pulse oximetry system 250 can include one or more devices or apparatuses to facilitate collection of the light 232 after it has been attenuated by the tissue site 106. For example, as illustrated in FIG. 2, the sensor 104 can include a lens 284, which can collect attenuated light exiting, reflecting off, and/or refracting off the tissue site and can focus the light the detector 208. In some cases, the lens 284 can advantageously focus the light 232 onto a smaller area such that the detector 208 can include fewer detectors to detect the light, which can increase an amount of light received by the detector 208. In some cases, the lens 284 advantageously allows the sensor 104 to use fewer or smaller detectors to capture the same amount of light. It will be understood that other optical elements can be utilized to increase the amount of light received by the detector 208. For example, in some cases, multiple lenses or one or more meta-materials can be positioned between the detector 208 and the tissue site 106 to increase an amount of light received by the detector 208.

In some cases, the sensor 104 can include a reflectance pulse oximetry system 260 configured for reflectance pulse oximetry. For example, the reflectance pulse oximetry system 260 can include an emitter 210 and a detector 208. The emitter 210 can emit light 234 to the tissue site 106. The light 234 emitted by the emitter 210 can include one or more of a plurality of wavelengths, such as Red, Infrared, or near-infrared wavelengths or wavelengths in the visible light spectra. The detector 208 can sense the light 234 emitted by the emitter 210 after it reflects and/or refracts off the tissue site 106. The detector 208 can generate one or more composite analog light intensity signals responsive to the light sensed by the detector 208. As illustrated in FIG. 2, in some cases, the detector 208 and the emitter 210 are proximate each other. For example, if the tissue site 106 is a forearm, the detector 208 can be positioned on one side of the forearm and the emitter 210 can be positioned on the same side of the forearm.

In some cases, the reflectance pulse oximetry system 260 can include one or more optical elements to increase an amount of light received by the detector 208. For example, as illustrated in FIG. 2, the reflectance pulse oximetry system 260 can include a lens 286 positioned between the emitter 210 and the tissue site 106. In some cases, at least some of the light 234 from the emitter 210 passes through the lens 286 and the lens 286 focuses the light 234, thereby increasing strength of the light signal and increasing an amount of light received by the detector 208. Similarly, as described herein, the reflectance pulse oximetry system 260 can include the lens 284 to facilitate collection of the light 234 after the light 234 has reflected and/or reflected off the tissue site 106. It will be understood that other optical elements can be utilized to increase an amount of light received by the detector 208. For example, in some cases, multiple lenses or one or more meta-materials can be positioned between the emitter 210 and the tissue site 106 to increase an amount of light received by the detector 208.

In some cases, the sensor 104 can include a plurality of sensors. For example, the sensor 104 can include a sensor that includes a transmission pulse oximetry system 250 and a sensor that includes a reflectance pulse oximetry system 260. In some cases, detector 208 is configured to receive light from each of the emitters 202 and 210. For example, the emitters 202, 210 may be configured to emit light during non-overlapping time periods. In some cases, detector 208 can include two or more detectors, such as one for detecting light from emitter 202 and one for detecting light from emitter 210. In some cases, the emitter 202 can be multiplexed with the emitter 210, and after collecting this data from the detector 208, converted to separate streams of data.

As described herein, in some cases, the reflectance pulse oximetry system 260 generates a higher intensity light 234 than the transmission pulse oximetry system 250 generates. This can be due at least in part to the fact that the light 232 emitted from the emitter 202 must traverse a longer path through the tissue site 106, while the light 234 emitted from the emitter 210 does not need to traverse as long of a path in the tissue site 106. Accordingly, in some cases, the reflectance pulse oximetry system 260 can operate at lower power than the transmission pulse oximetry system 250. For example, the emitter 210 can utilize less energy than emitter 202. Accordingly, in some cases, the reflectance pulse oximetry system 260 can be operated more than the transmission pulse oximetry system 250. For example, in some cases, the reflectance pulse oximetry system 260 can be operated continuously, while the transmission pulse oximetry system 250 is operated periodically. In some cases, the reflectance pulse oximetry system 260 can be utilized for a measurement of PR and/or PRV, while the transmission pulse oximetry system 250 is used for other measurements.

The DSP 212 can communicate with the sensor 104 via driver(s)/multiplexer(s) 216 and the front-end 214. For example, the DSP 212 can provide the driver(s)/multiplexer(s) 216 with digital control signals and the driver(s)/multiplexer(s) 216 can convert digital control signals into analog drive signals capable of driving emitters 202, 210. In some cases, the driver(s)/multiplexer(s) 216 act as a multiplexer and can select which emitter 202 or 210, if any, to drive or turn on. Furthermore, the DSP 212 can receive the one or more signals generated by the detector 208 via the front-end 214. In some cases, the signals generated by the detector 208 are light intensity signals indicative of one or more physiological parameters of the patient. For example, the signals can include a signal indicative of an amount or percentage of light reflected, absorbed, or transmitted at a tissue site 106.

The front-end 214 can convert the one or more composite analog light intensity signals from the detector 208 into digital data and input the digital data into the DSP 212. The digital data from the front-end 214 can correspond to at least one of a plurality of physiological parameters as described herein. For example, the digital data from the front-end 214 can be representative of a change in the absorption of particular wavelengths of light as a function of the changes in the tissue site 206 resulting from pulsing blood.

The DSP 212 can include one or more data or signal processors configured to execute one or more programs for determining physiological parameters from input data. The DSP 212 can perform operations that include calculating and outputting one or more physiological measures, such as $SpO_2$, PR, PRV, Pi, SpHb®, SpOC™, PVi®, SpMet®, SpCO®, or RRa®, or other parameters described herein. The operations performed by the DSP 212 can be implemented in software, firmware or other form of code or instructions, or logic or other hardware, or a combination of the above.

The DSP 212 can communicate with one or more input or output devices 220. The one or more input or output devices 220 can include a user interface 222, controls 224, a transceiver 226, and a memory device 228.

The user interface 222 can include a numerical or graphical display that provides readouts of measures or parameters, trends and bar graphs of measures or parameters, visual indications that measures are, say, above a threshold, visual indicators like LEDs of various colors that signify measure magnitude, or device management interfaces, which can be generated by LEDs, LCDs, or CRTs, for example. The user interface 222 can include an audible output device that provides readouts or audible indications that measures are, say, above a threshold. The user interface 222 can include one or more input devices like a keypad, touch screen, pointing device, voice recognition device, and computer that can be used to supply control or configuration data, such as initialization settings, from the user interface 222 to the instrument manager 210. In some implementations, the user interface 222 can be an interface for devices as well as users.

The controls 224 can be outputs to medical equipment, such as drug administration devices, ventilators, or fluid Ws, so as to control the amount of administered drugs, ventilator settings, or the amount of infused fluids. The patient monitor 102 can use the controls 224 to automatically treat the patient (for instance, provide fluid to the patient, provide medication to the patient, turn on a fan to cool the patient, or adjust a temperature of a room to heat or cool the patient) in response to determining that the patient may benefit from treatment.

The transceiver 226 via an antenna can transmit information about operation of the patient monitor 102 to an electronic device or receive control or configuration data for operating the patient monitor 102. The transceiver can, for example, communicate via a computer network or intermediary device or directly with the electronic device using electromagnetic radiation.

The memory device 228 can be used to store information about operation of the patient monitor 102. This information can, for example, include readouts of measures or parameters, trends and bar graphs of measures or parameters, visual indications or indicators.

One or more of the components relating to signal acquisition and/or processing (for example, front end 214, drivers/multiplexer 216, DSP 212, etc.) can be incorporated into one or more connecting cables, the sensors themselves, or are otherwise closer to the sensor sites. As such, in some cases, the patient monitor 102 can primarily include the input or output devices 220, while the sensor 104 can include components related to signal acquisition and/or processing. By reducing the number of components included in the patient monitor 102, 202, the monitor can, in some instances, be smaller in size and/or more portable, which can be more convenient for home or "spot check" use. Although some of the components are illustrated as single units, in some cases these components can be separated into two or more components. For example, the system 200 can include a front end, driver, or DSP for each of the emitters and/or detectors.

Although not illustrated in FIG. 1 or 2, patient monitor 102 or cables connecting the patient monitor 102 to the sensor 104 can further include one or more outputs that supply the signal(s) from the sensor 104 to one or more other electronic devices for further processing. As one example, signal(s) from the sensor 104 can be output in parallel by the sensor 104 or the cables that couple the sensor 104 to the patient monitor 102. In another example, the patient monitor 102 can include one or more outputs for outputting copy(ies) of the signal(s) from the sensor 104. In some instances, the copy(ies) of the signal(s) may be adjusted relative to the original(s) with filtering, scaling, or other changing prior to being provided to the one or more other electric devices.

Figure 3:
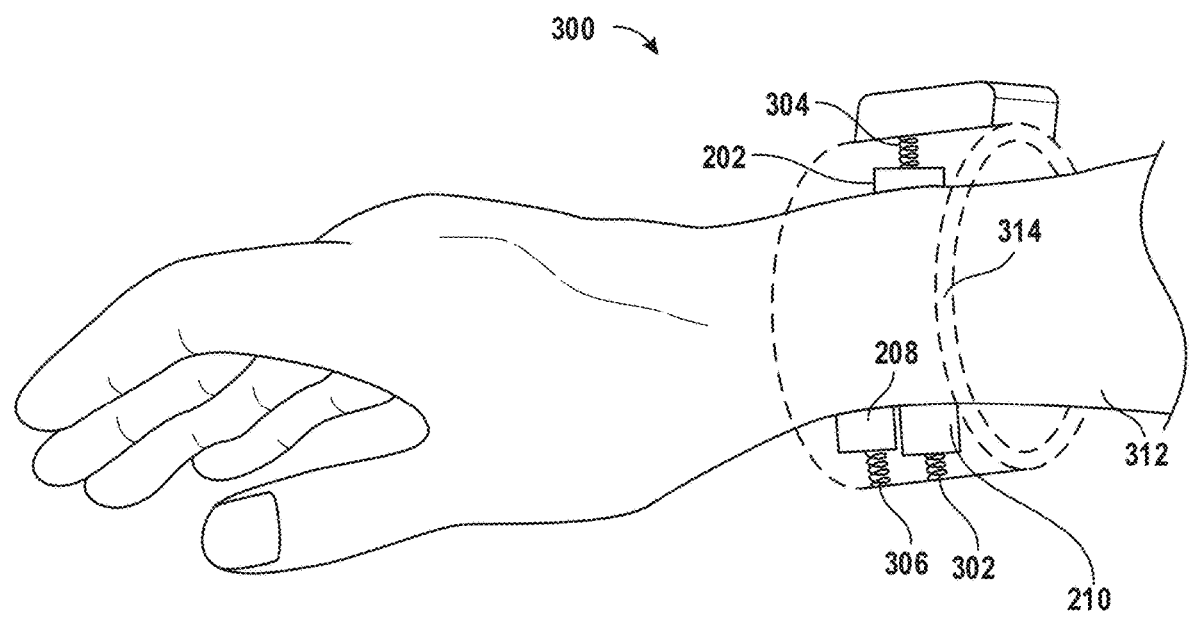
FIG. 3 illustrates an example patient monitoring device.

FIG. 3 illustrates an example patient monitoring device 300. The patient monitoring device 300 can be an embodiment of the patient monitoring system 100 or 200, or a subset thereof. As illustrated, the patient monitoring device 300 can include a first emitter 202, a second emitter 210, a detector 208, a wearable housing 314, and a plurality of resilient members 302, 304, 306. In the illustrated embodiment, the wearable housing 320 is shown as being worn the patient's wrist or forearm. However, the size or shape of the wearable housing 320 can vary across embodiments such that the wearable housing 320 can be configured to be worn on other areas, such as, but not limited to, an ankle, lower leg, knee, upper leg, upper arm, or the like.

As described herein, the first emitter 202 and the second emitter 210 can each be configured to emit light. For example, the emitters 202, 210 can be configured to transmit optical radiation having red, infrared (IR), near IR, wavelengths in the visible light spectra or another wavelength into tissue. The detector 208 can be configured to receive light after the light interacts with the tissue. For example, the detector 208 can receive light emitted from the first emitter 202 after the light passes through the tissue. As another example, the detector 208 can receive light emitted from the second emitter 210 after the light reflects or refracts off of the tissue.

In this example, the tissue includes the forearm 312 of the patient's right arm. As illustrated, the first emitter 202 and detector 208 are aligned on or within the wearable housing 314 such that at least some of the light that is emitted from the first emitter 202 travels between the radial and ulnar bones in the forearm 312 and is received by the detector 208. In some cases, as the light from the first emitter 202 passes through the radial and ulnar bones, some of the light is absorbed or otherwise does not pass through the tissue. The detector 208 can generate a signal responsive to the intensity of the light it receives after the light travels between the radial and ulnar bones and is attenuated by the tissue. Based at least in part on this signal, a processor can determine one or more physiological parameters.

Furthermore, in the illustrated example, the second emitter 210 is aligned with the detector 208 such that the detector 208 can receive at least some of the light that is emitted from the second emitter 210 after the light from the second emitter 210 is reflected or refracted by the tissue. The detector 208 can generate a signal responsive to the intensity of the reflected and/or refracted light. Based at least in part on this signal, a processor can determine one or more physiological parameters.

The patient monitoring device 300 can include one or more resilient members 302, 304 or 306. For example, in the illustrated embodiment, the resilient members 302, 304 or 306 are springs that are coupled to the emitter 210, emitter 202, and detector 208, respectively. In this example, the resilient members 302, 304 or 306 make the emitter 210, emitter 202, and detector 208 spring loaded, which allows for flexible or dynamic vertical, linear, or other movement by the emitter 210, emitter 202, and detector 208. For example, each of the resilient members 302, 304 or 306 can exert a force on its respective emitter 210, emitter 202, or detector 208. In some cases, the force exerted by the resilient members 302, 304 or 306 can be in a direction of the tissue. In other words, the resilient members 302, 304 or 306 can extend the emitter 210, emitter 202, and detector 208 towards the forearm 312 so that the emitter 210, emitter 202, and detector 208 can achieve good coupling with the forearm 312. In some cases, the resilient members 302, 304 or 306 can allow up to about 2, 5, 10, or 20 mm of movement by the emitters 202, 210 or the detector 208.

In some cases, the resilient members 302, 304 or 306 can allow the emitter 210, emitter 202, and detector 208 to stay in constant contact with the patient's forearm 312 as long as the patient is wearing the housing 314. For example, the housing 314 can be approximately fitted to the size of the patient's forearm 312 such that the patient's forearm 312 pushes back against the emitter 202, emitter 210, or detector 208 while the patient is wearing the housing 314.

In some cases, one or more of the resilient members 302, 304 or 306 are coupled to housing 314 to the emitter 210, emitter 202, or detector 208. In some cases, when the user wears the housing 314, the patient's forearm 312 is sufficiently close to the housing 314 such that the patient's forearm 312 presses back against the emitter 210, emitter 202, or detector 208 to compress the resilient member 302, 304 or 306 between the emitter 210, emitter 202, or detector 208 and the housing 314. While the spring the resilient member 302, 304 or 306 is compressed between the housing 314 and the emitter 202, the resilient member 302, 304 or 306 exerts a force on the emitter 210, emitter 202, or detector 208 in a direction towards the forearm 312 of the patient. In some cases, as long as the patient's forearm 312 is closer to the housing 314 than the size of the resilient member 302, 304 or 306 (e.g., a length of a spring), the resilient member 302, 304 or 306 will exert the force on the emitter 210, emitter 202, or detector 208 to cause the emitter 210, emitter 202, or detector 208 to stay in contact with the forearm 312.

Figure 4A:
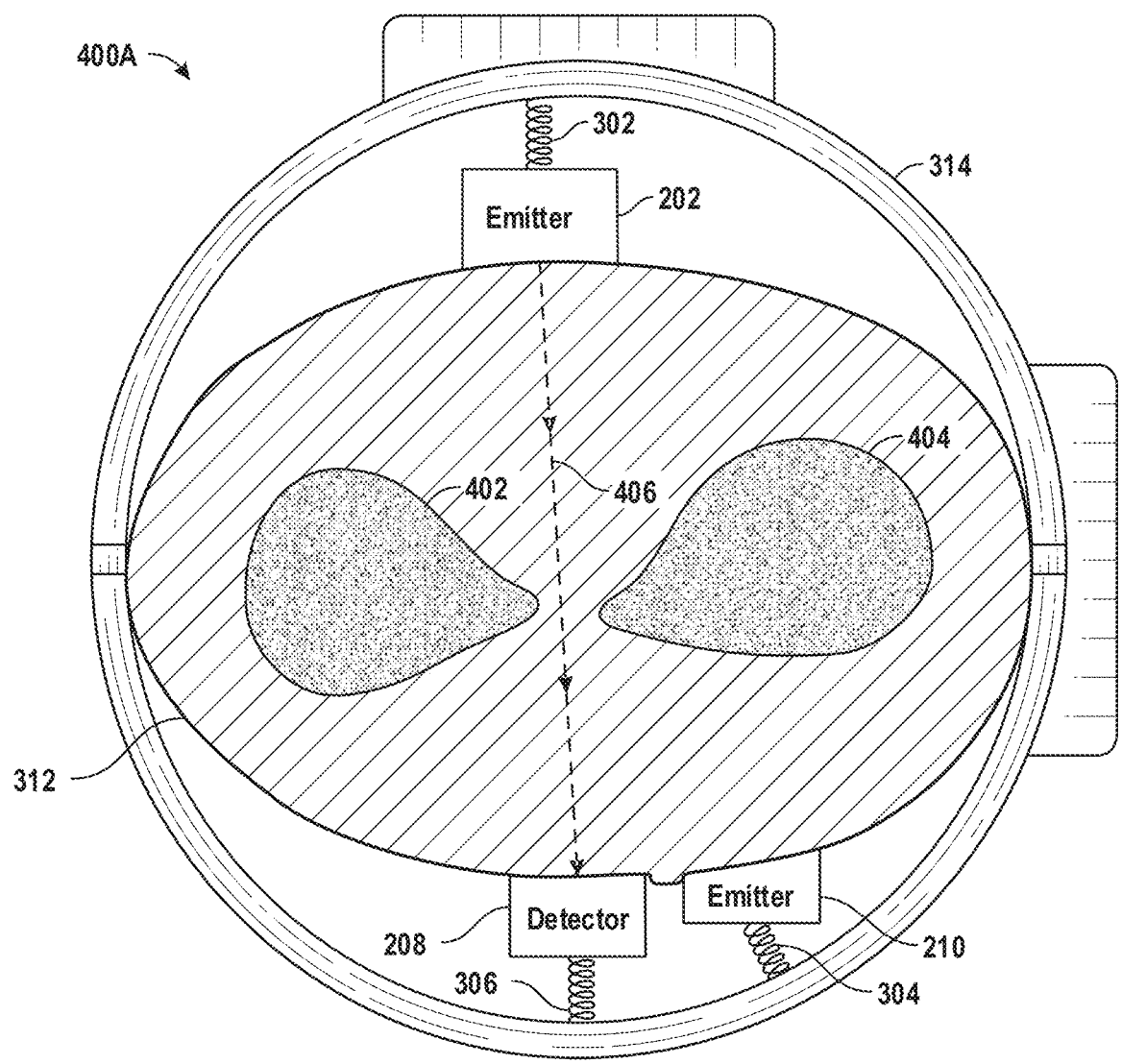
FIGS. 4A-4B illustrates a pictorial representation of a cross section of an example patient monitoring device being worn by a patient.

FIG. 4A illustrates a pictorial representation of a cross section of an example patient monitoring device 400A being worn by a patient. The patient monitoring device 400 can be an embodiment of the patient monitoring system 100 or 200, the patient monitoring device 300, or a subset thereof. As described herein, the patient monitoring device 400 can include a first emitter 202, a second emitter 210, a detector 208, a wearable housing 314, and a plurality of resilient members 302, 304 or 306. In this example, the wearable housing 304 is coupled around the forearm 312 of a patient, and the plurality of resilient members 302, 304 or 306 include a plurality of springs.

As illustrated, the first emitter 202 and the detector 208 are positioned in or on the housing 314 such that when the housing 314 is worn by the patient, the first emitter 202 and the detector 208 are aligned to transmit light 406 through the tissue site (e.g., the forearm 312), between the radial 404 and ulnar 402 bones in the forearm 312. However, in some cases, it may be appropriate to transmit light from the emitter 202 in a direction other than between the radial 404 and ulnar 402 bones. For example, the first emitter 202 and the detector 208 can be aligned so as to substantially avoid the light from the first emitter 202 colliding with any bones of the tissue site.

In some cases, the physiological monitoring system 400, such as the pulse oximetry sensor itself or an associated processor, can monitor and/or detect an alignment between the first emitter 202 and the detector 208. Alignment in this instance can include, but is not limited to, a determination that the detector 208 is oriented or positioned to receive light from the first emitter 202. Alignment can additionally or alternatively include a determination that the first emitter 202 and the detector 208 are aligned with an opening between bones. Alignment can additionally or alternatively include a determination that the first emitter 202 and the detector 208 are aligned such that no bones are in the way of the light path. In some cases, based at least in part on the monitored and/or detected alignment or misalignment, the physiological monitoring system can cause a notification to be delivered to the patient or a caregiver. For example, physiological monitoring system can notify (for example, via vibration, an audible noise, via a display, etc.) the patient or caregiver when the first emitter 202 and the detector 208 are not aligned.

As described herein, the resilient members 302, 304 or 306 can, among other things, ensure good contact between the emitter 210, emitter 202, or detector 208 and the patient's skin. Furthermore, the resilient members 302, 304 or 306 can facilitate a coupling of the emitter 210, emitter 202, or detector 208 with the patient's skin without requiring that the wearable housing 304 be tightly secured on the forearm, thereby avoiding a risk of injury or occlusion of blood flow. For example, housing 314 could be configured to fit loosely on the patient's arm, and the resilient member(s) can ensure that the emitter 210, emitter 202, or detector 208 make contact with patient's tissue, despite the loose fit of the housing 314. In some cases, although forearms come in various shapes and sizes, the resilient members 302, 304 or 306 can allow a particular device to fit on various sizes of forearms. Accordingly, in some cases, the utilization of one or more resilient members 302, 304 or 306 can allow for a production of fewer housing sizes. For example, the device can be a one-size fits all, one-size fits most, etc.

Figure 4B:
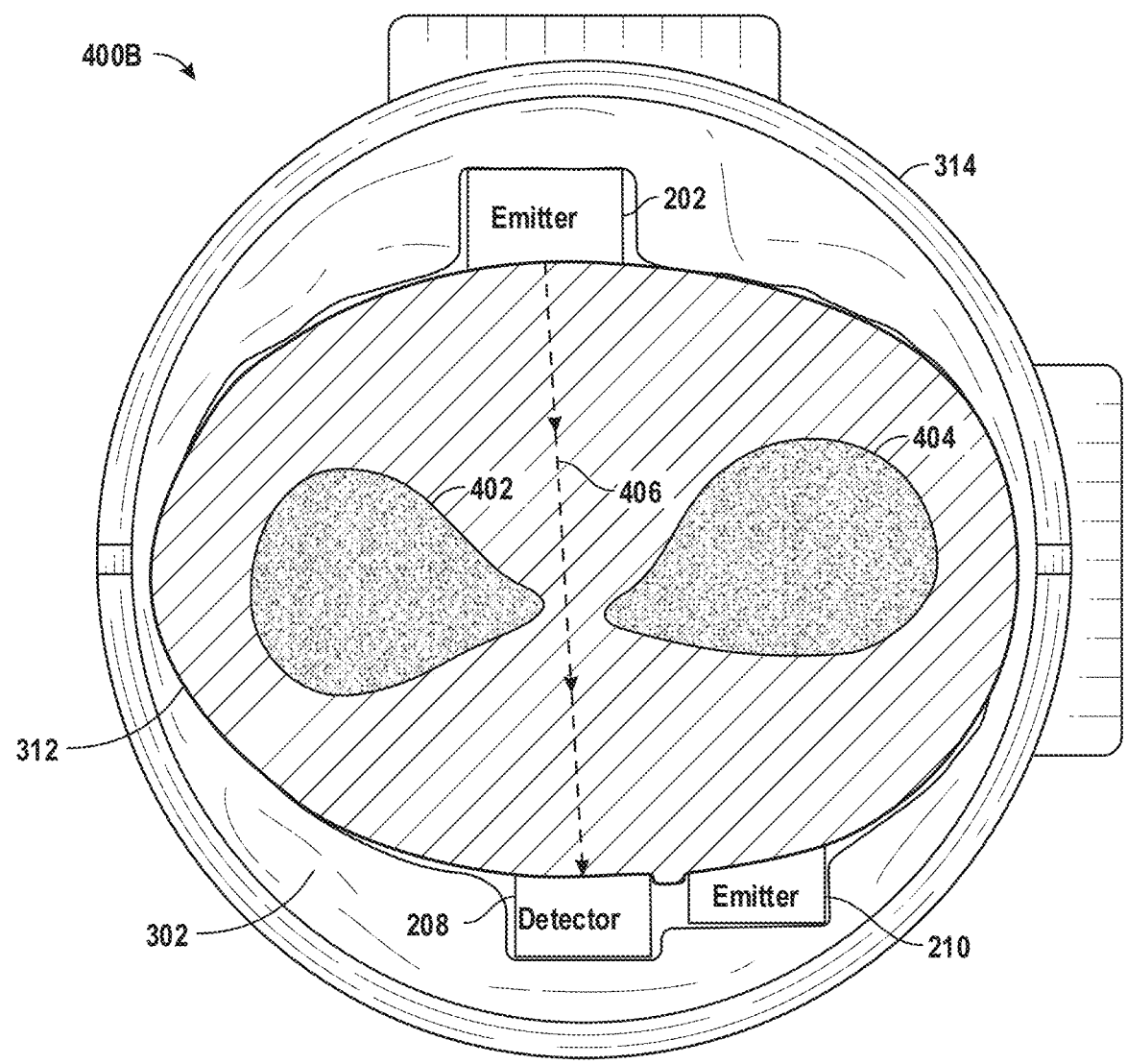

Although FIGS. 3 and 4A illustrated the resilient members 302, 304 or 306 as springs, the resilient members 302, 304 or 306 can include various other resilient members and/or mechanisms, such as, but not limited to, an inflatable bladder or a foam pad. For example, FIG. 4B illustrates a pictorial representation of a cross section of an example patient monitoring device 400B that includes an inflatable bladder as the resilient member 302. For example, as illustrated, the inflatable bladder can be coupled between the housing 314 and the emitter 210, emitter 202, or detector 208. Furthermore, the inflatable bladder can be inflated by a user to securely couple at least one of the emitter 210, emitter 202, or detector 208 to the forearm. In some cases, the inflatable bladder can also secure the housing 314 to the forearm so that the housing 314 is less likely to rotate about or slide along the forearm.

Similar to a resilient member 302, 304 or 306, in some cases, the patient monitoring device 400A or 400B can include various other elements that facilitate good contact between the detector 208, emitter 202, or emitter 210 and the patient's skin. For example, the patient monitoring device 400A or 400B can include a magnetic element that is configured to provide an opposing magnetic force to the detector 208, emitter 202, or emitter 210 to keep it in contact with the patient's skin. Similarly, one or more portions of the housing 314 can be configured to inflate, thereby causing the detector 208, emitter 202, or emitter 210 to retain contact with the patient's skin. For example, the housing can include one or more inflatable portions that, when inflated (for example, by an air pump), cause the housing to expand and the detector 208, emitter 202, or emitter 210 to contact the patient's skin.

Figure 5A:
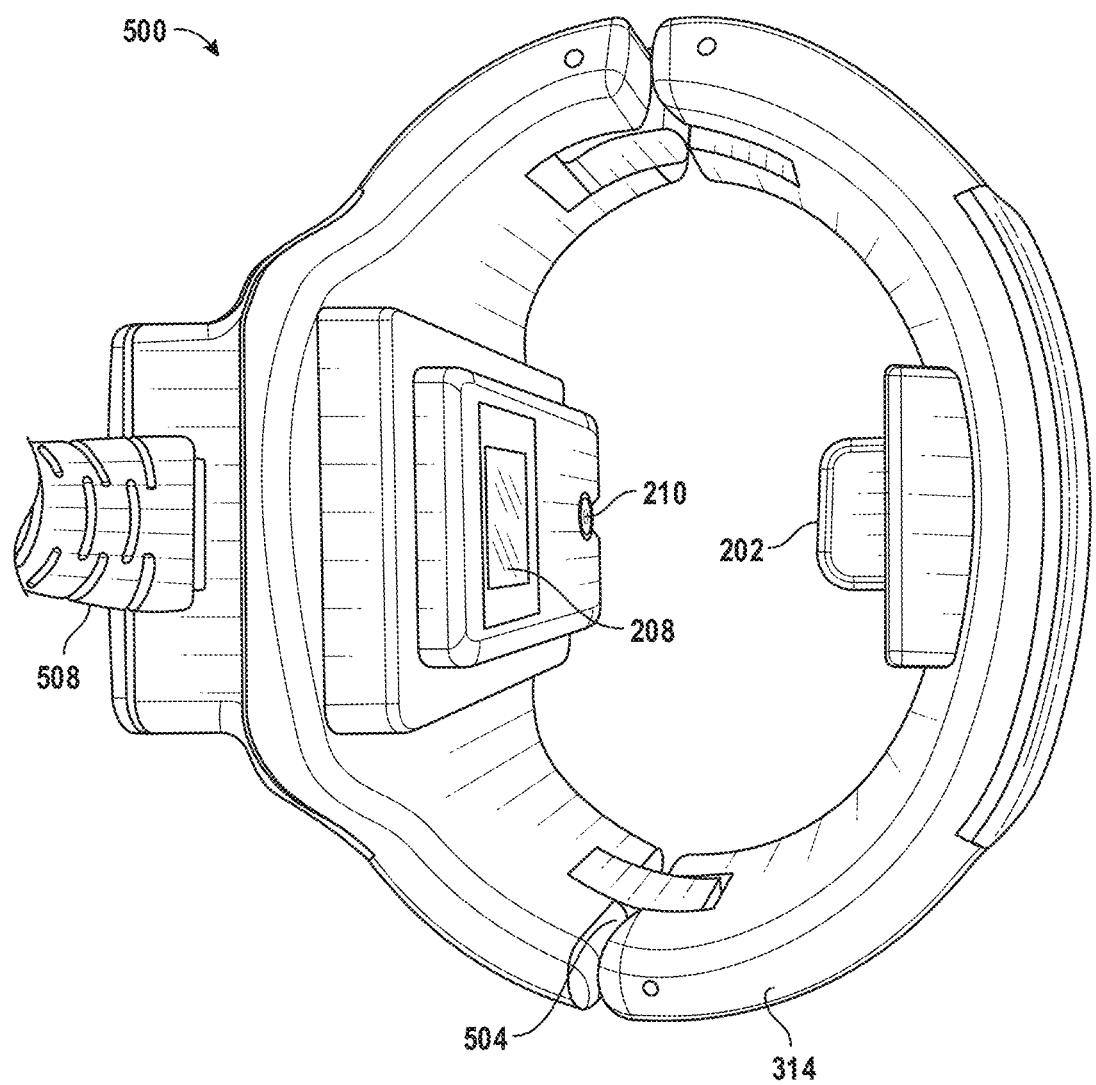
FIGS. 5A-5B illustrate an example patient monitoring device.
Figure 5B:
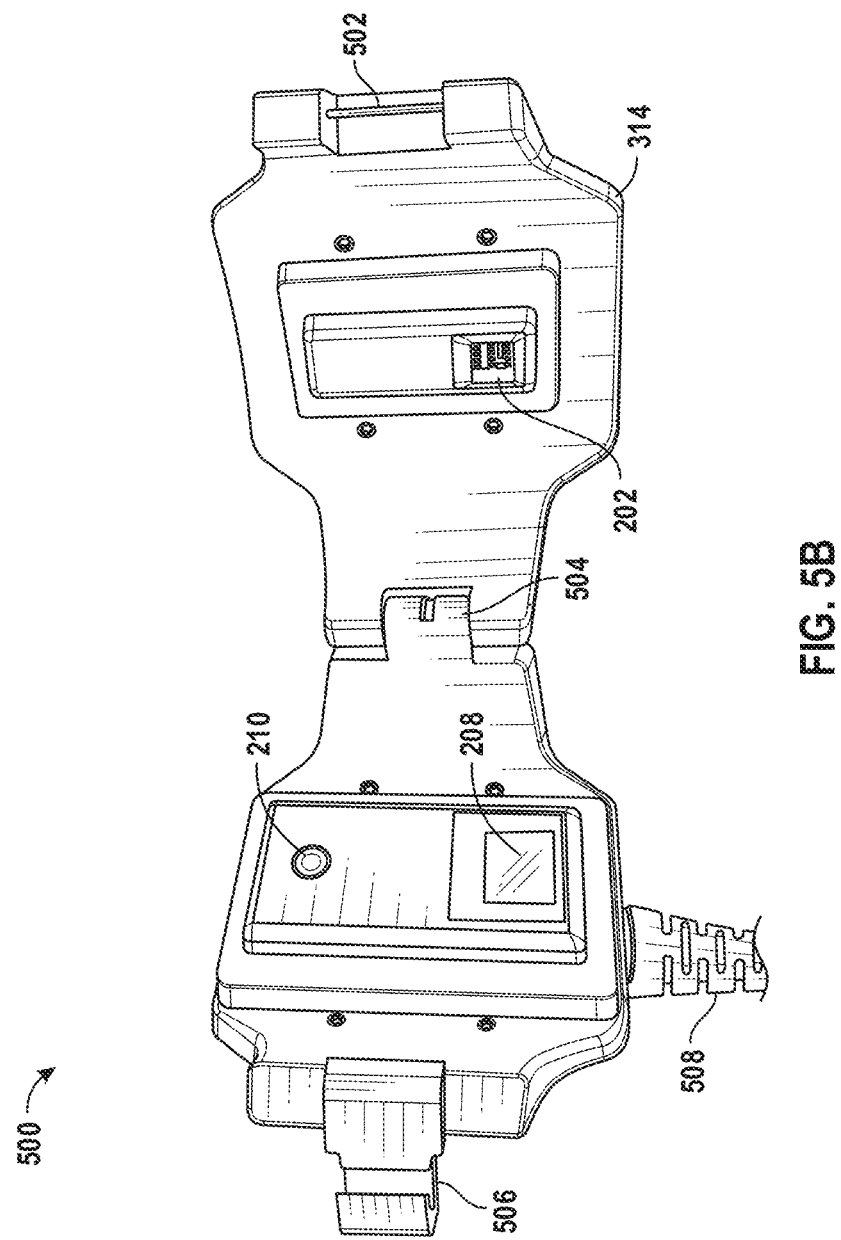

FIGS. 5A-5B illustrate an example patient monitoring device 500. As described herein, the patient monitoring device 500 can include an emitter 202, an emitter 210, and a detector 208. Furthermore, the patient monitoring device 500 can include a hinge 504 and fastening portions 502, 506.

As described herein, the detector 208 can be implemented as a Large Area Detector (LAD), which can incorporate a larger surface area as compared to typical photodetectors. For example, the path length through a forearm is an order of magnitude higher than a path length through a fingertip. This larger path length can result in increased scattering effects. The larger surface area of the LAD can allow the detector 208 to gather light scatter over a larger area, which can improve the received signal, either from emitter 202 or emitter 210.

As described herein, due to the higher absorption and scattering effects associated with the forearm, it may be advantageous to utilize an emitter 202 that can emit a higher light output than that of traditional emitters incorporated in fingertip pulse oximeters. Thus, the emitter 202 can be implemented as one or more high efficiency LEDs, such as those configured to emit light at Red (e.g., about 660 nm), Infrared (e.g., about 905 nm), or near Infrared wavelengths, or wavelengths in the visible light spectra.

The higher absorption of Red light as compared to Infrared light can be further accentuated by the larger path length at the forearm (as compared to the path length at a finger). Thus, in some cases, multiple Red (e.g., 660 nm) LEDs are connected in series to generate sufficient light that can traverse through the forearm. Similarly, the emitter 210 can be an LED, such as a high efficiency LED.

The housing 314 of the patient monitoring device 300 can be rigid such that the housing is relatively inflexible and/or stiff. In some cases, the housing 314 can include movable joint or hinge 504, which can ensure that the emitter 202 and detector 208 are aligned when the housing 314 is snapped closed via fastening portions 502, 506. For example, at least a portion of the housing 314 can swing on hinge 504 and the housing 314 can be closed via fastening portions 502, 506. The shape of the housing 314 and/or the position of the joint 504 can be designed such that the patient monitoring device 500 fits securely on the patient. For example, the housing 314 can have a generally oval shape that corresponds to a shape of the patient's forearm, and the hinge 504 can be located such that it will be positioned on a side of the patient's forearm when the patient monitoring device 500 is worn by the patient. This shape of the housing 314 and placement of the hinge 504 can allow for a secure fit on the patient's arm, while also aligning the emitter 202 and detector 208. For example, the emitter 202 and the detector 208 can be aligned such that a light path from the emitter 202 to the detector 208 does not hit any bones in the measurement site.

In some cases, the patient monitoring device 500 performs a calibration and can successfully calibrate when the emitter 202 and detector 208 are appropriately aligned. For example, the emitter 202 and detector 208 can be appropriately aligned when aligned opposite to each other when the housing 314 is worn around the forearm. For example, the patient monitoring device 500 can identify or determine one or more expected profiles for a ratio of the collected wavelengths. At least one profile can include a range of expected ratios or wavelengths that correspond to instances when the detector 208 and emitter 202 are properly aligned (e.g., the light path is not obstructed by bone). The system or device can collect and or determine alignment data in real-time and can compare the alignment data to the one or more profiles to determine if alignment is good, acceptable, unacceptable, or the like.

The illustrated example of FIGS. 5A and 5B further include a cable 508 configured to provide communication between the patient monitoring device 500 and a data collection system. For example, the patient monitoring device 500 can include a processor that can determine various physiological parameters based at least in part on signals from the detector 208. A data collection system (not shown) can connect to the patient monitoring device 500 via cable 508 to retrieve at least an indication of a physiological parameter. In some cases, communication between patient monitoring device 500 and a data collection system can be over wireless communications (e.g., Wi-Fi, Bluetooth, Cellular, etc.).

Physiological Parameter Determination

Figure 6:
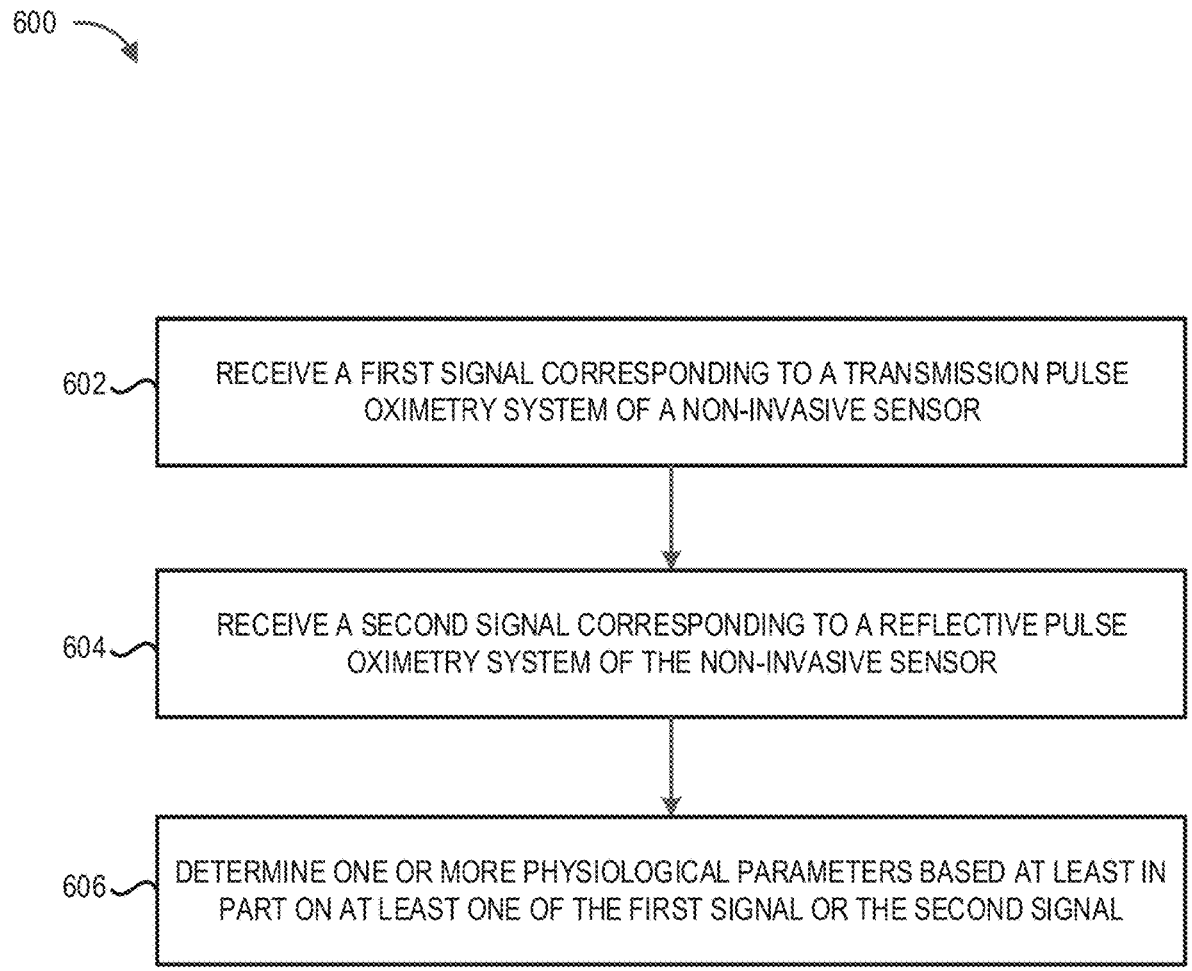
FIG. 6 illustrates an example flow diagram for determining a physiological parameter.

FIG. 6 illustrates a flow diagram illustrative of an embodiment of a routine implemented by a patient monitoring system for determining a physiological parameter. One skilled in the relevant art will appreciate that the elements outlined for routine 600 may be implemented by one or many computing devices or components, such as in hardware, with a front end component, with a sensor interface, or with a processor, such as one or more processors housed in a patient monitor, one or more remote processors, one or more processors housed in a limb-worn sensor, etc. Accordingly, routine 600 has been logically associated as being generally performed by a processor 100, and thus the following illustrative embodiments should not be construed as limiting.

At block 602, a processor 100 receives a first signal corresponding to a transmission pulse oximetry system of a non-invasive sensor, such as transmission pulse oximetry system 250 FIG. 2. As described herein, the non-invasive sensor can be part of a warble apparatus, such as patient monitoring device 300, 400A, 400B, or 500 that can worn by the patient, such as on a patient's wrist, forearm, elbow, upper arm, ankle, lower leg, back of the knee, or upper leg.

At block 604, the processor 100 receives a second signal corresponding to a reflective pulse oximetry system of a non-invasive sensor, such as reflective pulse oximetry system 260 FIG. 2.

At block 606, the processor can determine one or more physiological parameters based at least in part on at least one of the first signal or the second signal. For example, as described herein, the processor can determine $SpO_2$, PR, PRV, Pi, SpHb®, SpOC™, PVi®, SpMet®, SpCO®, or RRa®, among other physiological parameters. As described herein, in some cases, the transmission pulse oximetry system consumes more power than the reflectance pulse oximetry system. Thus, in some cases, the reflectance pulse oximetry system can be utilized more often than the transmission pulse oximetry system. For example, the reflectance pulse oximetry system can be used continuously or at a higher frequency than the transmission pulse oximetry system.

Depending on the embodiment, certain acts, events, blocks, communications or functions identified above can be performed in a different sequence, can be added, merged, or left out altogether (non-limiting example: not all described operations or events are necessary). For example, block 604 may additionally or alternatively occur prior to or currently with any of events 602 or 606. In addition, in some cases, any one or any combination of events 602, 604, or 606 can be omitted. Furthermore, any one or any combination of the activities described above can occur automatically and/or without user input.

Embodiments of the present disclosure can be described in view of the following clauses:

Clause 1. A wearable patient monitoring device configured to be worn on a forearm of a user, the patient monitoring device comprising:

a housing configured to attach at least partially around the forearm of the user, wherein a shape of the housing limits radial movement of the patient monitoring device about the forearm;

an emitter configured to emit light through tissue of the forearm;

a detector configured to sense the light after it passes through and is attenuated by the tissue and to generate a signal indicative of the sensed light, a first resilient member configured to exert a first force on the emitter, wherein the first force is in a direction of the tissue with respect to the emitter; and a second resilient member configured to exert a second force on the detector, wherein the second force is in a direction of the tissue with respect to the detector, wherein the housing is configured to support the emitter, the detector, the first resilient member, and the second resilient member, wherein when the housing is attached at least partially around the forearm the emitter and detector are aligned such that the light from the emitter travels through an opening between radial and ulnar bones of the forearm prior to being sensed by the detector.

Clause 2. A wearable patient monitoring device comprising:

an emitter configured to emit light; and a detector configured to sense the light after it passes through and is attenuated by tissue of a patient and to generate a signal indicative of the sensed light, wherein, when the patient monitoring device is attached to the patient, the emitter and detector are aligned such that the light from the emitter travels through an opening between a first bone and a second bone of the patient prior to being sensed by the detector.

Clause 3. The wearable patient monitoring device of any of the previous clauses, wherein the tissue corresponds to a forearm of the patient, wherein the first bone comprises a radial bone of the forearm and the second bone comprises an ulna bone of the forearm.

Clause 4. The wearable patient monitoring device of any of the previous clauses, wherein the tissue corresponds to a lower leg of the patient, wherein the first bone comprises a tibia bone of the lower leg and the second bone comprises a fibula bone of the lower leg.

Clause 5. The wearable patient monitoring device of any of the previous clauses, wherein the emitter is proximate to the tissue relative to the detector.

Clause 6. The wearable patient monitoring device of any of the previous clauses, further comprising a resilient member configured to exert a force on at least one of the emitter or the detector, wherein the force is in a direction of the tissue with respect to the at least one of the emitter or the detector.

Clause 7. The wearable patient monitoring device of any of the previous clauses, wherein the resilient member comprises a spring coupled to the at least one of the emitter or the detector.

Clause 8. The wearable patient monitoring device of any of the previous clauses, wherein the resilient member comprises an inflatable bladder, wherein the inflatable bladder is configured to inflate to secure the at least one of the emitter or the detector to the forearm.

Clause 9. The wearable patient monitoring device of any of the previous clauses, further comprising a hinge on which at least a portion of the patient monitoring device is configured to swing.

Clause 10. The wearable patient monitoring device of any of the previous clauses, wherein the patient monitoring device is configured to attach completely around at least one of a forearm of the patient or a lower leg of the patient.

Clause 11. The wearable patient monitoring device of any of the previous clauses, wherein a shape of the patient monitoring device comprises at least one of an oval-shape or an elliptical shape, wherein the shape of the patient monitoring device limits radial movement about forearm of the patient.

Clause 12. The wearable patient monitoring device of any of the previous clauses, wherein the detector comprises a large area photodetector.

Clause 13. The wearable patient monitoring device of any of the previous clauses, wherein the emitter is a first emitter and the light is first light, the patient monitoring device further comprising a second emitter configured to emit second light towards the tissue, wherein the detector is configured to detect the second light after it is reflected, refracted, or both by the tissue and to generate a signal indicative of the sensed second light.

Clause 14. The wearable patient monitoring device of any of the previous clauses, further comprising a multiplexor configured to select between the first emitter and the second emitter, wherein the selection causes the selected one of the first emitter or the second emitter to turn on.

Clause 15. The wearable patient monitoring device of any of the previous clauses, wherein the second emitter consumes less energy to emit the first light than the first emitter consumes to emit the second light.

Clause 16. The wearable patient monitoring device of any of the previous clauses, further comprising a lens, wherein at least a portion of the light passes through the lens.

Clause 17. The wearable patient monitoring device of any of the previous clauses, wherein the lens is positioned between the tissue site and at least one of the emitter or detector.

Clause 18. The wearable patient monitoring device of any of the previous clauses, wherein the lens is configured to increase an amount of the light received by the detector.

Clause 19. A wearable patient monitoring device comprising:
a transmission pulse oximetry system configured to emit first light and generate a first signal;
a reflective pulse oximetry system configured to emit second light and generate a second signal, wherein power consumed by the reflective pulse oximetry system to emit the second light is less than power consumed by the transmission pulse oximetry system to emit the first light; and
a processor in communication with the transmission pulse oximetry system and the transmission pulse oximetry system, the processor configured to determine a physiological parameter based at least in part on at least one of the first signal or the second signal.

Clause 20. The wearable patient monitoring device of any of the previous clauses, wherein the physiological parameter comprises at least first and second physiological parameters, wherein the processor is configured to determine the first physiological parameter based at least in part on the first signal, wherein the processor is configured to determine the second physiological parameter based at least in part on the second signal.

Clause 21. The wearable patient monitoring device of any of the previous clauses, wherein the first physiological parameter comprises at least one of blood oxygen saturation ($SpO_2$) or pulse rate (PR), and wherein the second physiological parameter comprises pulse rate variability (PRV).

Clause 22. The wearable patient monitoring device of any of the previous clauses, wherein the transmission pulse oximetry system comprises:
a first emitter configured to emit first light through tissue of a patient, and
a first detector configured to sense the first light after it passes through and is attenuated by the tissue and to generate the first signal, wherein the first signal is indicative of the sensed first light.

Clause 23. The wearable patient monitoring device of any of the previous clauses, wherein the transmission pulse oximetry system further comprises a lens, wherein at least a portion of the light passes through the lens.

Clause 24. The wearable patient monitoring device of any of the previous clauses, wherein the lens is positioned between the tissue and at least one of the first emitter or first detector.

Clause 25. The wearable patient monitoring device of any of the previous clauses, wherein when the patient monitoring device is attached to the patient, the first emitter and the first detector are aligned such that the first light from the first emitter travels through an opening between a first bone and a second bone of the patient prior to being sensed by the first detector.

Clause 26. The wearable patient monitoring device of any of the previous clauses, wherein the tissue corresponds to a forearm of the patient, wherein the first bone comprises a radial bone of the forearm and the second bone comprises an ulna bone of the forearm.

Clause 27. The wearable patient monitoring device of any of the previous clauses, wherein the tissue corresponds to a lower leg of the patient, wherein the first bone comprises a tibia bone of the lower leg and the second bone comprises a fibula bone of the lower leg.

Clause 28. The wearable patient monitoring device of any of the previous clauses, wherein the reflective pulse oximetry system comprises:
a second emitter configured to emit second light to tissue of a patient, and
a second detector configured to sense the second light after it is reflected and/or refracted at the tissue and to generate second signal, wherein the second signal is indicative of the sensed second light.

Clause 29. The wearable patient monitoring device of any of the previous clauses, wherein the reflective pulse oximetry system further comprises a lens, wherein at least a portion of the light passes through the lens.

Clause 30. The wearable patient monitoring device of any of the previous clauses, wherein the lens is positioned between the tissue and at least one of the second emitter or second detector.

Clause 31. The wearable patient monitoring device of any of the previous clauses, further comprising a housing configured to attach at least partially around at least a portion of a limb of a patient.

Clause 32. The wearable patient monitoring device of any of the previous clauses, wherein the at least a portion of the limb comprises at least one of a forearm of the patient or a lower leg of the patient.

Clause 33. The wearable patient monitoring device of any of the previous clauses, wherein first physiological parameter is different from the second physiological parameter.

Clause 34. A patient monitoring device comprising:
an emitter configured to emit light;
a detector configured to sense the light after it interacts with tissue of a patient and further configured to generate a signal indicative of the sensed light;
a housing supporting the emitter and the detector and configured to attach at least partially around at least a portion of a limb of a patient; and
a resilient member coupled between the housing and at least one of the emitter or the detector, wherein the resilient member is configured to exert a force on the at least one of the emitter or the detector, wherein the force is in a direction of the tissue with respect to the at least one of the emitter or the detector.

Clause 35. The patient monitoring device of any of the previous clauses, wherein, when the housing is attached to the patient, the emitter and the detector are aligned such that the light from the emitter travels through an opening between a first bone and a second bone of the patient prior to being sensed by the detector.

Clause 36. The patient monitoring device of any of the previous clauses, wherein the tissue corresponds to a forearm of the patient, wherein the first bone comprises a radial bone of the forearm and the second bone comprises an ulna bone of the forearm.

Clause 37. The patient monitoring device of any of the previous clauses, wherein the tissue corresponds to a lower leg of the patient, wherein the first bone comprises a tibia bone of the lower leg and the second bone comprises a fibula bone of the lower leg.

Clause 38. The patient monitoring device of any of the previous clauses, wherein the detector is configured to sense the light after it passes through the tissue and is attenuated by the tissue.

Clause 39. The patient monitoring device of any of the previous clauses, wherein the detector is configured to sense the light after it reflects and/or refracts off the tissue.

Clause 40. The patient monitoring device of any of the previous clauses, wherein the resilient member comprises a spring.

Clause 41. The patient monitoring device of any of the previous clauses, wherein the resilient member comprises an inflatable bladder, wherein the inflatable bladder is configured to inflate to couple the at least one of the emitter or the detector to the tissue.

Clause 42. A system comprising the device of any one or more of the preceding clauses.

Clause 43. A method comprising:
receiving a signal corresponding to a transmission pulse oximetry system of a wearable patient monitoring device, wherein the transmission pulse oximetry system comprises:
an emitter configured to emit light through tissue of a patient, and
a detector configured to sense the light after it passes through and is attenuated by the tissue and to generate the signal indicative of the sensed light,
wherein, when the wearable patient monitoring device is worn by the patient, the emitter and detector are aligned such that the light from the emitter travels through an opening between a first bone and a second bone of the patient prior to being sensed by the detector; and
determining a physiological parameter based at least in part on the signal.

Clause 44. The method of clause 43, wherein the signal is a first signal, the emitter is a first emitter, and the light is first light, the method further comprising:
receiving a second signal corresponding to a reflective pulse oximetry system of the wearable patient monitoring device, wherein the reflective pulse oximetry system comprises:
a second emitter configured to emit second light to the tissue of a patient, and
the detector, wherein the detector is further configured to sense the second light after it is reflected and/or refracted at the tissue prior to being received by the detector and to generate the second signal indicative of the sensed second light,
wherein said determining the physiological parameter is further based at least in part on the second signal.

Clause 45. The method of any of clause 43 or 44, wherein the second emitter consumes less energy than the first emitter.

Clause 46. The method of any of clauses 43-45, wherein the tissue corresponds to a forearm of the patient, wherein the first bone comprises a radial bone of the forearm and the second bone comprises an ulna bone of the forearm.

Clause 47. The method of any of clauses 43-46, wherein the tissue corresponds to a lower leg of the patient, wherein the first bone comprises a tibia bone of the lower leg and the second bone comprises a fibula bone of the lower leg.

Clause 48. The method of any of clauses 43-47, wherein the detector comprises a large area photodetector.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The foregoing description is merely illustrative in nature and is in no way intended to limit the disclosure, its application, or uses. For purposes of clarity, in some cases, the same reference numbers will be used in the drawings to identify similar elements. It should be understood that steps within a method may be executed in different order without altering the principles of the present disclosure.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Depending on the embodiment, certain operations, acts, events, or functions of any of the algorithms described herein can be performed in a different sequence, can be added, merged, or left out altogether (non-limiting example: not all are necessary for the practice of the algorithms). Moreover, in certain embodiments, operations, acts, functions, or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based at least in part on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based at least in part on the language employed in the claims and not limited to the examples described in the present specification or during the prosecution of the application, which examples are to be construed as non-exclusive.

What is claimed is:

1. A wearable patient monitoring device comprising:
   an emitter configured to emit light towards a limb of a patient;
   a detector configured to sense the light after it passes through and is attenuated by tissue of the limb of the patient and to generate a signal indicative of the sensed light;
   a wearable housing configured to engage with the limb of the patient and to support the emitter and the detector, the wearable housing comprising a hinge and at least two rigid components coupled by the hinge, wherein a shape of the wearable housing is based at least in part on a placement of the hinge and shapes of the at least two rigid components, the shape of the wearable housing configured to:
      limit lateral or rotational movement about the limb; and
      facilitate alignment of a light path between the emitter and the detector with an opening between a first bone and a second bone of the limb of the patient; and
   a processor configured to receive the signal indicative of the sensed light to determine that the light path are not aligned with the opening between the first bone and the second bone of the limb of the patient based on the signal indicative of the sensed light and provide a notification to a user indicating misalignment.

2. The wearable patient monitoring device of claim 1, wherein the limb is a leg of the patient, wherein the first bone comprises a tibia bone of the leg, and wherein the second bone comprises a fibula bone of the leg.

3. The wearable patient monitoring device of claim 1, further comprising a biasing member that biases the emitter in a direction away from the wearable housing and towards the patient.

4. The wearable patient monitoring device of claim 3, wherein the biasing member is a spring.

5. The wearable patient monitoring device of claim 1, wherein the detector comprises a large area photodetector.

6. The wearable patient monitoring device of claim 1, wherein the emitter is a first emitter and the light is first light, the wearable patient monitoring device further comprising a second emitter configured to emit second light towards the tissue, wherein the detector is configured to detect the second light after it is reflected, refracted, or both by the tissue and to generate a signal indicative of the sensed second light.

7. The wearable patient monitoring device of claim 6, further comprising a multiplexor configured to select between the first emitter and the second emitter, wherein the selection causes the selected first emitter or second emitter to turn on.

8. The wearable patient monitoring device of claim 6, wherein the second emitter consumes less energy to emit the second light than the first emitter consumes to emit the first light.

9. The wearable patient monitoring device of claim 1, wherein the wearable housing reduces a likelihood that the wearable patient monitoring device is attached to the patient in an orientation other than that which orients the light path to be aligned with the opening.

10. The wearable patient monitoring device of claim 1, wherein the wearable housing further comprising a size configured to facilitate alignment of the light path.

11. The wearable patient monitoring device of claim 1, wherein the shape corresponds to an oval shape of the wearable housing.

12. The wearable patient monitoring device of claim 1, wherein the limb includes a forearm of the patient, wherein the hinge is configured to be positioned on a side of the forearm and adjacent to either a radial bone or an ulna bone.

13. A method comprising:
providing a wearable patient monitoring device that includes a wearable housing, a processor, an emitter, and a detector, the wearable housing comprising a hinge and at least two rigid components coupled by the hinge, wherein a shape of the wearable housing is based at least in part on a placement of the hinge and shapes of the at least two rigid components,
wherein during attachment of the wearable patient monitoring device to a limb of a patient the shape of the wearable housing is configured to limit lateral or rotational movement about the limb and facilitate alignment of a light path between the emitter and the detector with an opening between a first bone and a second bone of the limb of the patient,
wherein the processor configured to receive a signal indicative of a sensed light to determine that the light path is not aligned with the opening based on the signal indicative of the sensed light and provide a notification to a user;
receiving a signal from the detector, the signal being responsive to light emitted by the emitter and detected by the detector after the light passes through the opening between the first bone and the second bone; and
determining a physiological parameter based at least in part on the signal.

14. The method of claim 13, wherein the limb includes a forearm of the patient, wherein the first bone is a radial bone of the forearm, and wherein the second bone is an ulna bone of the forearm.

15. The method of claim 13, wherein the limb is a leg of the patient, wherein the first bone is a tibia bone of the leg, and wherein the second bone is a fibula bone of the leg.

16. The method of claim 13, wherein the wearable housing reduces a likelihood that the wearable patient monitoring device is attached to the patient in an orientation other than that which orients the light path to be aligned with the opening.

17. The method of claim 13, wherein the wearable housing corresponds to a size of the wearable patient monitoring device.

18. The method of claim 13, wherein the shape corresponds to an oval shape of the wearable patient monitoring device.

19. The method of claim 13, wherein the limb includes a forearm of the patient, wherein the hinge is configured to be positioned on a side of the forearm and adjacent to either a radial bone or an ulna bone.

* * * * *

UNITED STATES PATENT AND TRADEMARK OFFICE
CERTIFICATE OF CORRECTION

PATENT NO. : 11,766,198 B2
APPLICATION NO. : 16/265733
DATED : September 26, 2023
INVENTOR(S) : Kevin Hughes Pauley et al.

It is certified that error appears in the above-identified patent and that said Letters Patent is hereby corrected as shown below:

In the Drawings

Sheet 2 of 8, (Reference Numeral 212, FIG. 2), Line 2, delete "PROCESSORS(S)" and insert -- PROCESSOR(S) --.

In the Specification

Column 4, Line 15 (approx.), delete "$\epsilon b*c$" and insert -- $\epsilon*b*c$ --.

Column 10, Line 40, delete "Ws," and insert -- IVs, --.

Column 15, Line 11 (approx.), delete "and or" and insert -- and/or --.

In the Claims

Column 25, Line 22, Claim 13, delete "patient" and insert -- patient, --.

Signed and Sealed this
Fifth Day of December, 2023

Katherine Kelly Vidal
*Director of the United States Patent and Trademark Office*